US011647342B2

(12) United States Patent
Kuipers

(10) Patent No.: US 11,647,342 B2
(45) Date of Patent: May 9, 2023

(54) AVOIDANCE OF USER DISCOMFORT DUE TO PRESSURE DIFFERENCES BY VENT VALVE, AND ASSOCIATED SYSTEMS AND METHODS

(71) Applicant: Sonova AG, Stäfa (CH)

(72) Inventor: Erwin Kuipers, Wolfhausen (CH)

(73) Assignee: Sonova AG, Stäfa (CH)

( * ) Notice: Subject to any disclaimer, the term of this patent is extended or adjusted under 35 U.S.C. 154(b) by 0 days.

(21) Appl. No.: 17/714,897

(22) Filed: Apr. 6, 2022

(65) Prior Publication Data

US 2022/0232330 A1 Jul. 21, 2022

Related U.S. Application Data

(63) Continuation of application No. 17/085,825, filed on Oct. 30, 2020, now Pat. No. 11,343,616, which is a continuation of application No. 16/370,667, filed on Mar. 29, 2019, now Pat. No. 10,939,215.

(51) Int. Cl.
*H04R 25/00* (2006.01)
*A61B 5/00* (2006.01)

(52) U.S. Cl.
CPC ........... *H04R 25/30* (2013.01); *A61B 5/6817* (2013.01); *H04R 2225/61* (2013.01)

(58) Field of Classification Search
CPC .... H04R 25/30; H04R 2225/61; A61B 5/6817
See application file for complete search history.

(56) References Cited

U.S. PATENT DOCUMENTS

| 5,440,082 | A | 8/1995 | Claes | |
|---|---|---|---|---|
| 6,549,635 | B1 * | 4/2003 | Gebert | ................. H04R 25/652 381/322 |
| 8,241,224 | B2 | 8/2012 | Keefe | |
| 8,391,527 | B2 * | 3/2013 | Feucht | ................... H04R 25/65 381/328 |
| 8,923,543 | B2 * | 12/2014 | Sacha | ................. H04R 25/456 381/328 |
| 9,039,639 | B2 | 5/2015 | George et al. | |
| 9,185,504 | B2 | 11/2015 | Shennib et al. | |
| 9,779,716 | B2 | 10/2017 | Gadonniex et al. | |

(Continued)

FOREIGN PATENT DOCUMENTS

DE 19 942 707 A1 3/2001
EP 0 533 258 B1 5/1998
(Continued)

*Primary Examiner* — Oyesola C Ojo
(74) *Attorney, Agent, or Firm* — Christensen O'Connor Johnson Kindness PLLC

(57) ABSTRACT

Systems and methods are disclosed for avoidance of user discomfort due to pressure differences by vent valve. In one embodiment, a method for equalizing air pressure in ear canal includes sensing a pressure difference between a pressure in ear canal ($P_{EC}$) and an ambient pressure ($P_{AMB}$) by a sensor of a hearing device. Based on sensing the pressure difference, an active valve is set to a first position to open a vent through the hearing device or to a second position to close the vent through the hearing device.

20 Claims, 4 Drawing Sheets

(56) References Cited

U.S. PATENT DOCUMENTS

| | | |
|---|---|---|
| 10,582,285 B2 | 3/2020 | Valenzuela |
| 2004/0010181 A1* | 1/2004 | Feeley ................. H04R 25/60 |
| | | 381/322 |
| 2008/0194984 A1 | 8/2008 | Keefe |
| 2009/0316941 A1 | 12/2009 | Lowmiller et al. |
| 2012/0082335 A1* | 4/2012 | Duisters ............... H04R 1/1041 |
| | | 381/375 |
| 2012/0087528 A1* | 4/2012 | Higgins ............... H04R 25/554 |
| | | 381/329 |
| 2014/0153761 A1* | 6/2014 | Shennib ............... H04R 25/652 |
| | | 381/328 |
| 2014/0175525 A1* | 6/2014 | Feyh .................. B81C 1/00246 |
| | | 257/254 |
| 2015/0000678 A1* | 1/2015 | Buckler ................. A61F 11/12 |
| | | 128/867 |
| 2015/0003644 A1 | 1/2015 | George et al. |
| 2015/0047960 A1* | 2/2015 | Davis ..................... H01H 13/14 |
| | | 200/52 R |
| 2015/0092971 A1* | 4/2015 | Kim ....................... H04R 25/30 |
| | | 381/328 |
| 2016/0241967 A1* | 8/2016 | van 't Hof ............. H04R 25/30 |
| 2017/0193974 A1 | 7/2017 | Gadonniex et al. |
| 2019/0215621 A1* | 7/2019 | Albahri ................ H04R 25/405 |
| 2019/0246194 A1* | 8/2019 | Aase .................... H04R 25/305 |
| 2019/0246219 A1* | 8/2019 | Lafort ..................... H01F 7/064 |
| 2020/0196074 A1* | 6/2020 | Tiefenau ............. H04R 25/456 |
| 2020/0203812 A1* | 6/2020 | Murray ................... H01Q 9/285 |

FOREIGN PATENT DOCUMENTS

| | | |
|---|---|---|
| EP | 1 594 344 A3 | 3/2006 |
| EP | 1 865 843 A2 | 9/2006 |
| WO | 2006/101935 A3 | 3/2007 |
| WO | 2010/120243 A1 | 10/2010 |
| WO | 2012/044278 A1 | 4/2012 |
| WO | 2014/210457 A1 | 12/2014 |
| WO | 2015/009421 A1 | 1/2015 |
| WO | 2017/117295 A1 | 7/2017 |

* cited by examiner

AVOIDANCE OF USER DISCOMFORT DUE TO PRESSURE DIFFERENCES BY VENT VALVE, AND ASSOCIATED SYSTEMS AND METHODS

CROSS-REFERENCES TO RELATED APPLICATIONS

This application is a continuation of U.S. application Ser. No. 17/085,825, filed Oct. 30, 2020, which is a continuation of U.S. application Ser. No. 16/370,667, filed Mar. 29, 2019, now U.S. Pat. No. 10,939,215, the disclosures of which are expressly incorporated by reference in its entirety.

FIELD OF THE INVENTION

The present invention relates generally to hearing instruments, and more particularly relates to methods and apparatuses for avoiding a discomfort caused by pressure differences between the ambient air pressure and the air pressure in the ear canal. In particular, such discomfort may be related to an insertion and a removal of the hearing device.

BACKGROUND

Hearing devices (also referred to as "hearing aid devices" or "hearing aids") are designed to be worn continuously behind the ear or inside the ear for extended periods of time. FIG. 1 is a schematic view of a hearing device inside the ear canal in accordance with prior art. The illustrated prior art hearing device 300 seals the cavity between the eardrum and the outside ambient as the housing of the hearing device laterally contacts the surrounding tissue of an ear canal 100. As a result, a relatively small sealed cavity is created between a medial end of the hearing device 300M and the eardrum 110. The pressure inside this sealed cavity is referred to as $P_{EC}$ (pressure in the ear canal). The pressure on the opposite, lateral end 300L of the hearing device is generally close to the ambient pressure, and is referred to as $P_{AMB}$.

Hearing devices must be accessed from time to time to, for example, adjust their settings, recharge the device, reprogram the device, etc. Typical hearing devices are removed from the ear on a daily basis (e.g., during the night). Rapid removal or insertion of the hearing device causes a correspondingly rapid decrease or increase of pressure in the cavity between the hearing device and the eardrum. Such rapid pressure changes cause users to experience discomfort, and may even rupture the eardrum. The discomfort can also be caused under other scenarios, for example, by changes in pressure during travelling by airplane or by rapid changes in elevation, for instance when traveling on a mountain gondola or in an elevator.

With some conventional technologies, the hearing device includes one or more vents that connect the medial end 300M with the lateral end 300L of the hearing device. However, such vents also affect the operating characteristics of the hearing device. For example, as the amplified sound is directed toward the eardrum, the sound waves reflect, partly back-propagating through the vent toward the lateral end 300L, and then impinging back on the microphone at the lateral end 300L of the hearing device, where the sound is again amplified. Such positive feedback amplification may quickly generate annoyingly high sound levels, comparable to the positive feedback problems that are sometimes experienced at large concert venues. Additionally, such vents tend to reduce fidelity of the low frequency sound.

Some other conventional technologies rely on flaps in the vents to reduce the above-described positive feedback. In operation, a pressure differential (if existing) forces the flap to open a path through the vent, resulting in the equalization of $P_{EC}$ with $P_{AMB}$. However, in operation, these flaps may get stuck in their open or closed position, which either disables their intended function (when stuck closed), or results in the positive feedback (when stuck open). Furthermore, even when operating as designed, flaps open and close at relatively small pressure differentials, therefore causing constant changes in the quality of the sound, as perceived by the user. For example, even one flight of stairs may be enough to open, and then close the vents, affecting the quality of sound, and therefore annoying the user. A further disadvantage of a flap-based design is that the vent is not fully sealed. Instead, a residual acoustic leakage remains.

Accordingly, there remains a need for reliable methods and systems for reducing user discomfort by pressure differences between the ambient pressure and the pressure in the ear canal, while preserving quality of the sound perceived by the user.

SUMMARY

This summary is provided to introduce a selection of concepts in a simplified form that are further described below in the Detailed Description. This summary is not intended to identify key features of the claimed subject matter.

The inventive technology is directed to the equalization of pressure in the cavity between the hearing device and the eardrum ($P_{EC}$) against the outside ambient pressure ($P_{AMB}$). As a result, user discomfort caused by these static pressure differences is reduced. In some embodiments, the medial end of the hearing device (facing the eardrum) is connected with the lateral side of the hearing device (facing the outside ambient) through a vent that has an active valve. In operation, the active valve is opened based on a pressure difference between $P_{EC}$ and $P_{AMB}$ exceeding a predetermined threshold value. During normal operation, the active valve may remain closed to reduce the positive feedback of sound and to improve the quality of sound. As a result, the highly discomforting experiences related to the insertion and removal of the hearing device (also referred to as "hearing aid" or "hearing aid device") may be reduced, while also avoiding the constant opening/closing of the vent that may annoy the user.

In some embodiments, the opening and closing of the active valve may be triggered by contact sensors on the surface of the hearing aid. For example, as the user touches the hearing device to insert or remove the device, a controller may drive the active valve into its open position to allow equalization between $P_{EC}$ and $P_{AMB}$.

In operation, removal of the hearing device from its charger typically precedes the insertion of the device in the ear by a short duration of time. Therefore, in some embodiments, when the device is disconnected from the charger or when the device is turned on, the controller triggers a period of time (e.g., 5-30 sec) during which the active valve remains open.

In one embodiment, a method for equalizing air pressure in the ear canal includes: sensing a pressure difference between a pressure in ear canal ($P_{EC}$) and an ambient pressure ($P_{AMB}$) by a sensor of a hearing device; and based on sensing the pressure difference, setting an active valve to a first position to open a vent through the hearing device or to a second position to close the vent through the hearing device.

In one aspect, the sensor is a differential pressure sensor configured to sense the pressure difference between the $P_{EC}$ and the $P_{AMB}$.

In another aspect, the sensor includes a first pressure sensor, configured to sense a first environmental condition corresponding to the $P_{EC}$ and a second sensor configured to sense a second environmental condition corresponding to the $P_{AMB}$. The method further includes determining a difference between the first environmental condition and the second environmental condition.

In one aspect, the method also includes: touching a touch sensor by a user; and in response to touching the touch sensor, setting the active valve to the first position to open the vent.

In one aspect, the method also includes: activating a timer of the hearing device; and in response to activating the timer, maintaining the active valve in its open state for a predetermined duration of time.

In one aspect, the predetermined duration of time is between 5 seconds and 30 seconds.

In another aspect, the timer is activated by removing the hearing device from a charging station.

In one aspect, the method also includes: inserting the hearing device into an ear of a user; emitting a test acoustic signal by a receiver of the hearing device; receiving a return acoustic signal by the receiver; and based on the return signal, determining whether the vent is closed.

In one aspect, the hearing device is selected from a group consisting of a completely-in-ear-canal (CIC) hearing device, a receiver-in-canal (RIC) hearing device, a behind-the-ear (BTE) hearing device, and an in-the-ear (ITE) hearing device.

In another aspect, the hearing device is selected from a group consisting of an audio reproduction device, a hearable, an earphone, and a hearing assistive device.

In one embodiment, a hearing device includes: a housing that comprises a vent connecting a medial side of the hearing device to a lateral side of the hearing device; at least one pressure sensor configured to sense a pressure difference between a pressure in ear canal ($P_{EC}$) of a user and an ambient pressure ($P_{AMB}$); and an active valve configured to open and close the vent based on a reading of the at least one sensor.

In one aspect, the at least one pressure sensor is a differential pressure sensor.

In one aspect, the at least one pressure sensor comprises a first sensor configured to sense the $P_{EC}$, and a second sensor configured to sense the $P_{AMB}$.

In one aspect, the hearing device also includes a touch sensor configured to sense handling of the hearing device.

In one aspect, the hearing device also includes a removal handle attached to the housing of the hearing device, where the removal handle carries the touch sensor.

In another aspect, the removal handle connects an in-the-ear piece with a behind-the-ear piece of the hearing aid device.

In one aspect, the hearing device also includes a timer configured to maintain the active valve in its open state for a predetermined duration of time.

In another aspect, the timer is activated by removing the hearing device from a charging station.

In one aspect, the hearing device also includes an acoustic receiver configured to amplify acoustic signals.

In one aspect, the hearing device is selected from a group consisting of a completely-in-ear-canal (CIC) hearing device, a receiver-in-canal (RIC) hearing device, a behind-the-ear (BTE) hearing device, and an in-the-ear (ITE) hearing device.

In another aspect, the hearing device is selected from a group consisting of an audio reproduction device, a hearable, an earphone, and a hearing assistive device.

In one aspect, the hearing device also includes a controller configured to receive readout data from the at least one sensor and to send control data to the active valve.

In one aspect, the hearing device also includes at least one movement detection sensor selected from a group consisting of an accelerometer, a gyroscope, a micro-electromechanical (MEMS) accelerometer and a MEMS gyroscope.

DESCRIPTION OF THE DRAWINGS

The foregoing aspects and the attendant advantages of the inventive technology will become more readily appreciated as the same become better understood by reference to the following detailed description, when taken in conjunction with the accompanying drawings, wherein.

DETAILED DESCRIPTION

The following disclosure describes various embodiments of systems and associated methods for in-ear acoustic readout of data from a hearing instrument. A person skilled in the art will also understand that the technology may have additional embodiments, and that the technology may be practiced without several of the details of the embodiments described below with reference to FIGS. 2-4.

Figure 1:
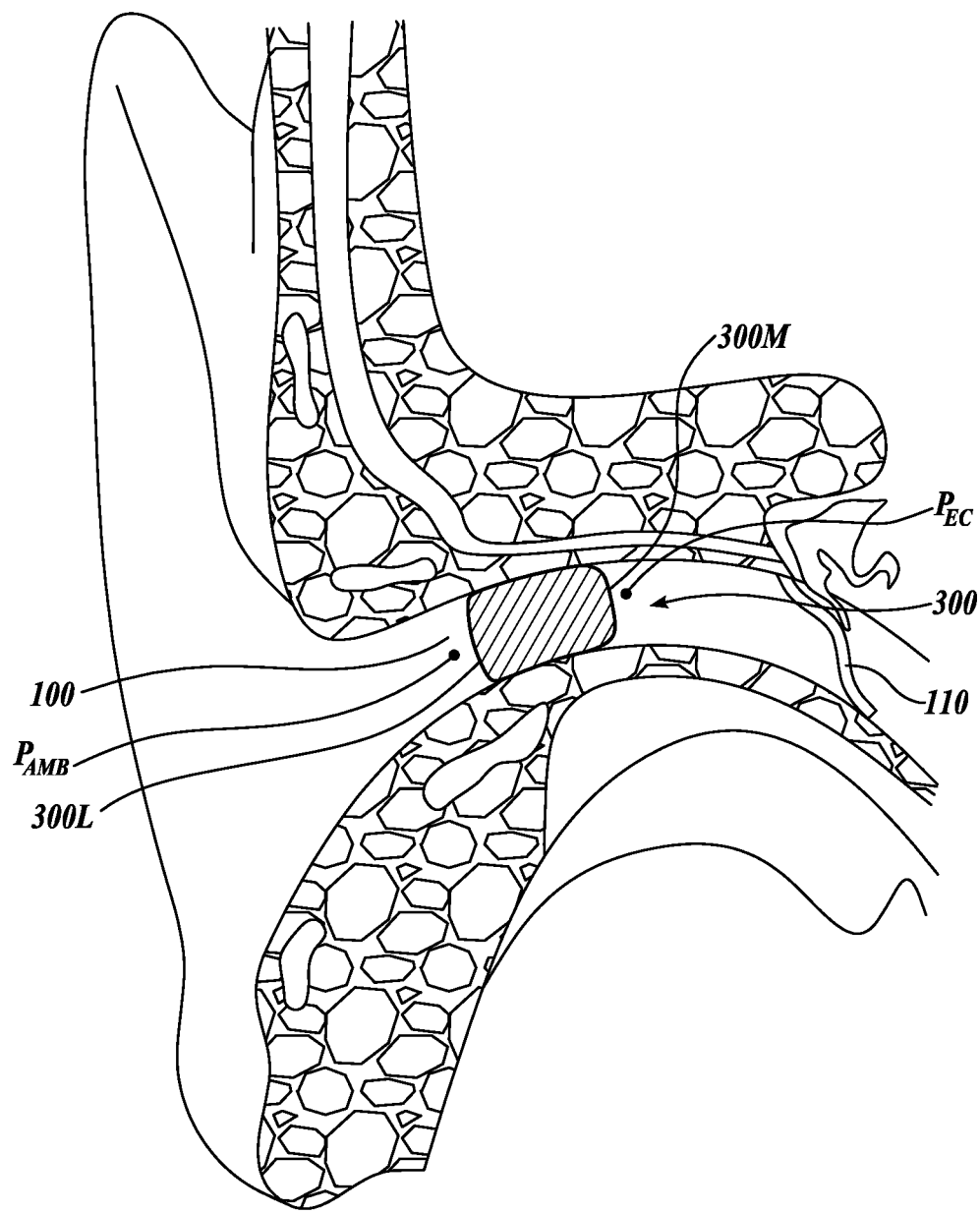
FIG. 1 is a schematic view of a hearing device inside an ear canal in accordance with prior art.
Figure 2:
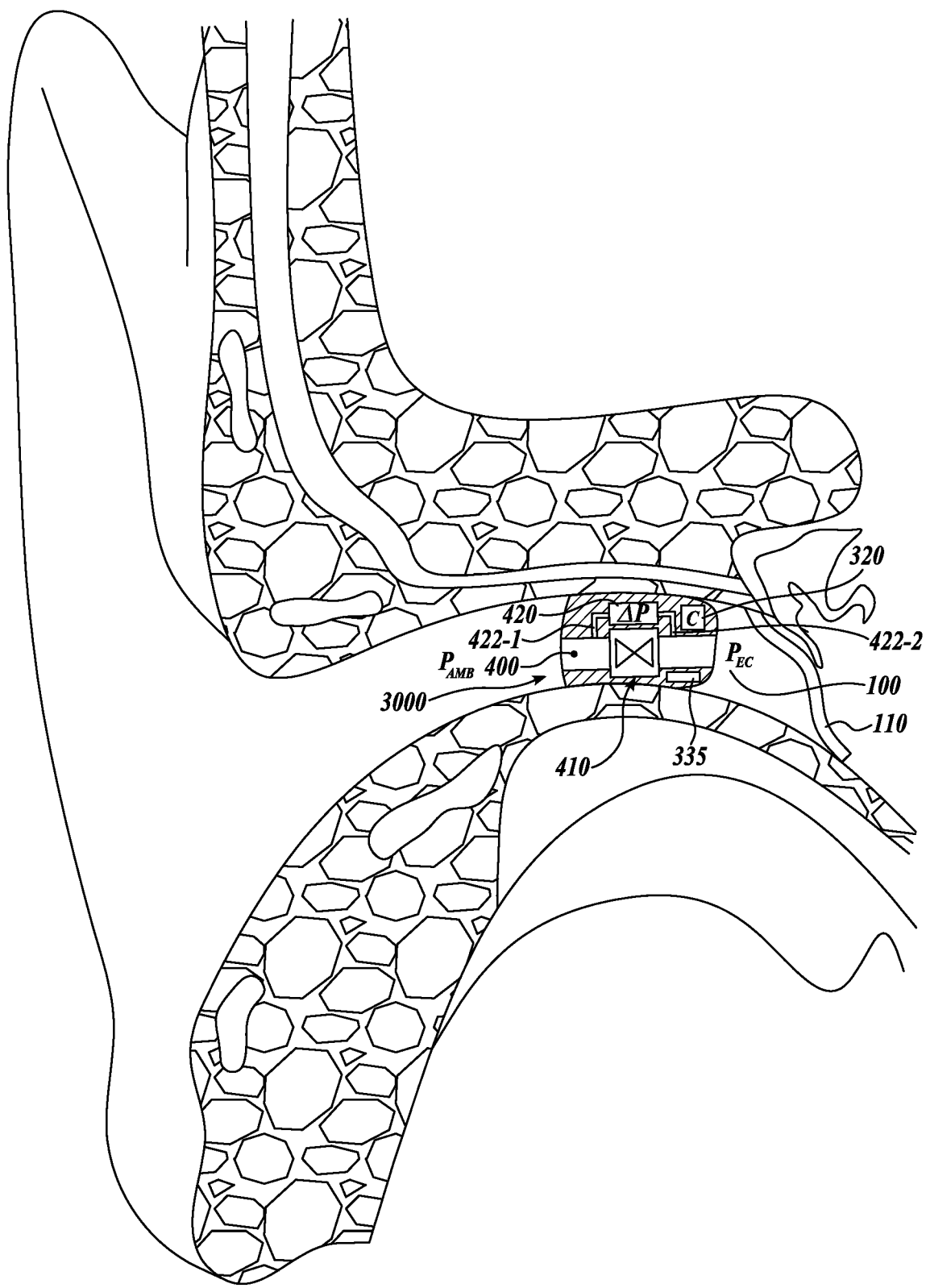
FIG. 2 is a schematic view of a hearing device inside the ear canal in accordance with an embodiment of the presently disclosed technology.

FIG. 2 is a schematic view of a hearing device 3000 inside the ear canal in accordance with an embodiment of the presently disclosed technology. When inserted into the ear canal 100, the hearing device 3000 seals the cavity against the eardrum 110. Therefore, pressure $P_{EC}$ in the sealed cavity may differ from the $P_{AMB}$ at the opposite side of the hearing device 3000, thus generating a net force on the hearing device which may hurt or annoy the user.

In some embodiments, the hearing device 3000 includes a vent 400 that connects the sealed cavity at $P_{EC}$ with the opposite, ambient side of the hearing device. In operation, a pressure sensor 420 measures the pressure difference between $P_{EC}$ and $P_{AMB}$, while an active valve 410 (also referred to as a "vent valve") keeps the vent 400 closed. In at least some embodiments, keeping the active valve 410 closed improves quality of sound that the user experiences. If the pressure difference between the $P_{AMB}$ and $P_{EC}$ ("environmental conditions") exceeds a predetermined threshold $P_{LIMIT}$, a controller 330 or other controlling unit of the hearing a device may send command data that opens the valve 410, thus enabling equalization between the $P_{AMB}$ and $P_{EC}$. As a result, the user experiences less discomfort when, for example, the hearing device is removed or inserted, or during other events that cause pressure differences between $P_{AMB}$ and $P_{EC}$ (e.g., during a flight). After the pressure is equalized between $P_{AMB}$ and $P_{EC}$, the valve 410 may close to, for example, maintain quality of sound transmission during operation of the hearing device 3000. In different embodiments, the value of predetermined threshold $P_{LIMIT}$ may be selected so as to not cause opening of the valve 410 during a small change in pressure (e.g., caused by a short elevator ride).

Some nonexclusive examples of the valve 410 include micro-electromechanical (MEMS) or miniature electromechanical valves. Some nonexclusive examples of the pressure sensors 420 include MEMS pressure sensors or differential pressure sensors. In some embodiments, the differential pressure sensor 420 may include two individual pressure sensors 422-1 and 422-2 each capable of sensing the absolute pressure. In operation, the controller 330 and the valve 410 may derive power from a battery 335.

While a completely-in-canal (CIC) hearing device is illustrated in FIG. 2, other types of the hearing devices are also within the bounds of this specification. Some nonexclusive examples of such hearing devices are receiver-in-canal (RIC), behind-the-ear (BTE) and in-the-ear (ITE) hearing devices. Furthermore, passive hearing protection plugs are included, when having suitable electrical power and controls. For example, when inserted, the hearing protection plugs seal the ear canal for improved sound isolation. However, this sealing increases the risk of discomfort, pain or even rupturing of the drum when inserting or removing the hearing protections plug. Other examples of the hearing devices include audio reproduction devices, hearables, earphones, hearing assistive devices and the like.

Figure 3:
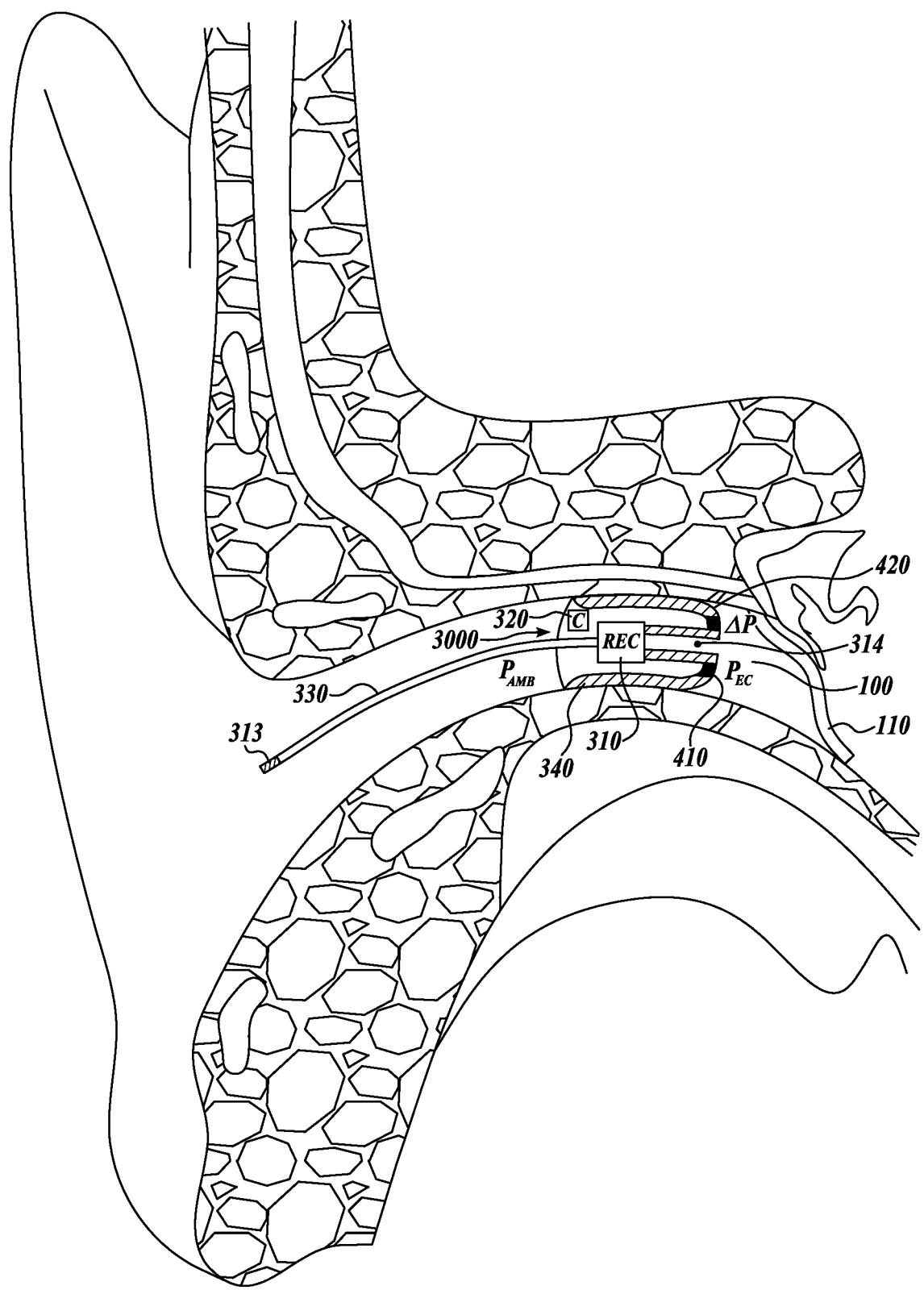
FIG. 3 is a schematic view of a hearing device inside the ear canal in accordance with an embodiment of the presently disclosed technology.

FIG. 3 is a schematic view of a hearing device 3000 inside the ear canal in accordance with an embodiment of the presently disclosed technology. The illustrated hearing device 3000 includes a receiver 310 that emits amplified sound waves through an opening 314. In some embodiments, a dome 340 of the hearing device 3000 carries a differential pressure sensor 420 (or two individual pressure sensors that collectively operate as a differential pressure sensor). The dome 340 may have a vent with the valve 410 that opens and closes based on a pressure difference between $P_{AMB}$ and $P_{EC}$.

In some embodiments, the hearing device includes a handle 330 (also referred to as a "cable" or a "removal handle") to assist insertion and removal of the device. In some embodiments, one or more touch sensors 313 are operationally connected with the controller 320 such that touching the sensor 313 activates the active valve 410 into its open position. In some embodiments, the handle 330 connects an in-the-ear piece with a behind-the-ear piece (not shown) of the hearing aid device. In different embodiments, one or more sensors 313 may be located on other parts of the hearing device 3000 that are contacted as the user handles the device.

In some embodiments, a removal of the hearing device 3000 from its charger generally precedes the insertion of the device in the ear by a short duration of time. Therefore, in some embodiments, when the hearing device is disconnected from the charger or when the device is turned on, the controller triggers a period of time (e.g., 5-30 sec) during which the active valve remains open.

In other embodiments 313, the sensors may be a hearing device microphone or a hearing aid ear canal microphone. In different embodiments, the sensors 313 that trigger the controller may include movement detection sensors, such as accelerometers or gyroscopes, for example MEMS accelerometers and MEMS gyroscopes. The pressure sensors, touch sensors, timers and other sensors (collectively, sensors 313) may trigger the active valve based on different physical parameters, as described above. These physical parameters are herein collectively referred to as the environmental conditions.

Figure 4:
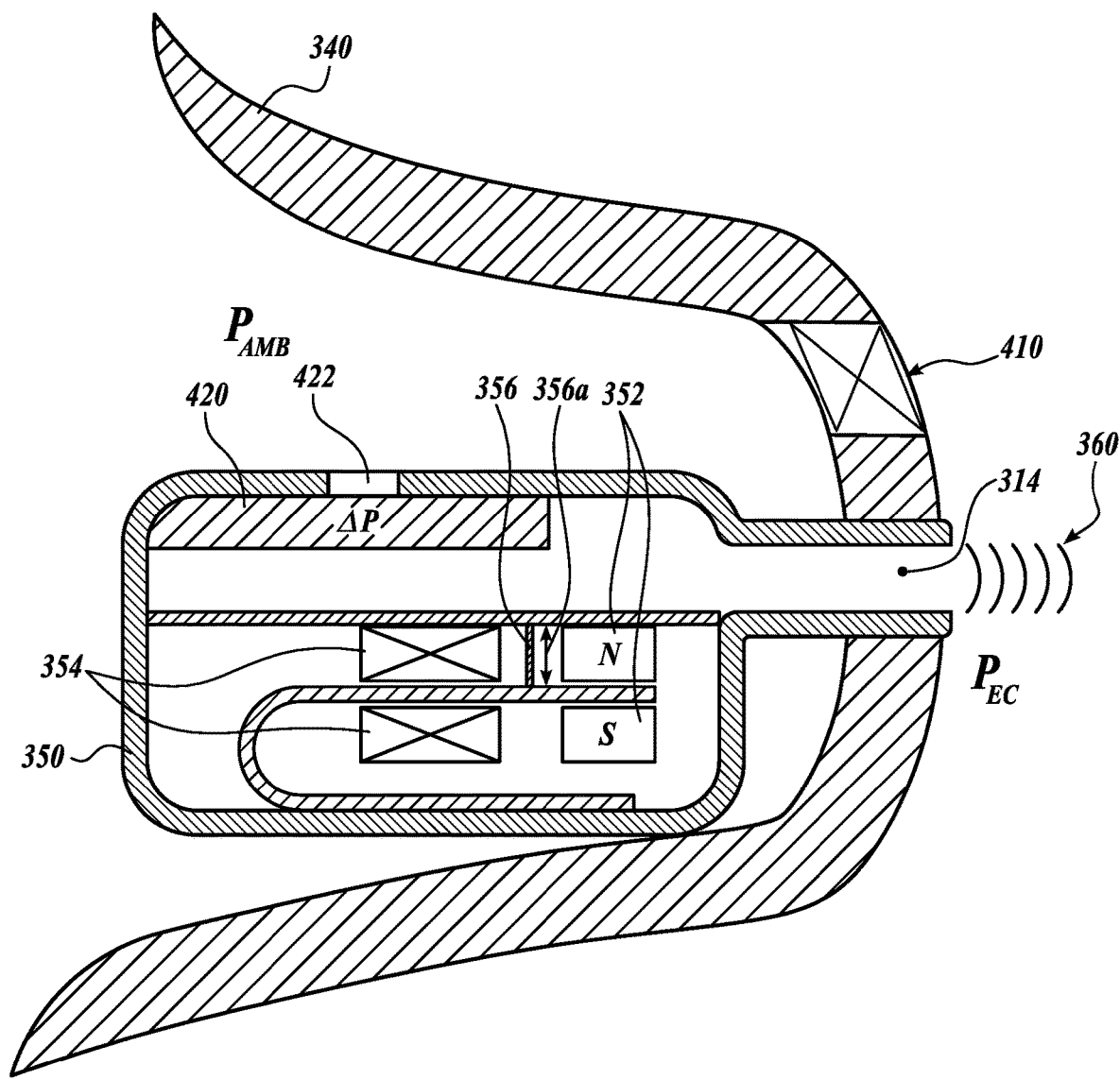
FIG. 4 is a schematic view of a receiver of a hearing device in accordance with an embodiment of the presently disclosed technology.

FIG. 4 is a schematic view of a receiver 350 of a hearing device in accordance with an embodiment of the presently disclosed technology. The illustrated receiver includes a pair of magnets 352 and an armature 354. In operation, the magnetic field created by the magnets 352 and the armature 354 forces an actuator 356 into actuation 356a, which, in turn, generates sound waves 360 that propagate toward the eardrum of the user.

In some embodiments, the receiver 350 may carry the pressure sensor 420. For example, one side of the differential pressure sensor 420 may be exposed to $P_{AMB}$ through a pressure sensing path 422 on the receiver, while the other side of the differential pressure sensor is exposed to $P_{EC}$ through the opening 314. In the illustrated embodiment, the active valve 410 opens and closes the vent that connects $P_{AMB}$ and $P_{EC}$.

Many embodiments of the technology described above may take the form of computer-executable or controller-executable instructions, including routines stored on non-transitory memory and executed by a programmable computer or controller. Those skilled in the relevant art will appreciate that the technology can be practiced on computer/controller systems other than those shown and described above. The technology can be embodied in a special-purpose computer, application specific integrated circuit (ASIC), controller or data processor that is specifically programmed, configured or constructed to perform one or more of the computer-executable instructions described above. In many embodiments, any logic or algorithm described herein can be implemented in software or hardware, or a combination of software and hardware.

From the foregoing, it will be appreciated that specific embodiments of the technology have been described herein for purposes of illustration, but that various modifications may be made without deviating from the disclosure. Moreover, while various advantages and features associated with certain embodiments have been described above in the context of those embodiments, other embodiments may also exhibit such advantages and/or features, and not all embodiments need necessarily exhibit such advantages and/or features to fall within the scope of the technology. Accordingly, the disclosure can encompass other embodiments not expressly shown or described herein.

I claim:

1. A hearing device, comprising:
   a housing that comprises a vent connecting a medial side of the hearing device to a lateral side of the hearing device;
   a removal handle attached to the housing of the hearing device;
   a touch sensor carried by the removal handle, wherein the touch sensor is configured to sense handling of the hearing device, wherein the touch sensor is operationally connected with a controller of the hearing device; and
   an active valve configured to open and close the vent based on an output of the touch sensor.

2. The device of claim 1, wherein the removal handle connects an in-the-ear piece with a behind-the-ear piece of the hearing device.

3. The device of claim 1, further comprising a timer configured to maintain the active valve in its open state for a predetermined duration of time.

4. The device of claim 3, wherein the timer is activated by removing the hearing device from a charging station.

5. The device of claim 1, further comprising:
at least one movement detection sensor configured to sense a movement of the hearing device within an ear canal, wherein the active valve is configured to open and close the vent at least in part based on an output of the at least one movement detection sensor.

6. The device of claim 5, wherein the at least one movement detection sensor is an accelerometer or a gyroscope.

7. The device of claim 6, wherein the accelerometer is a micro-electromechanical (MEMS) accelerometer and the gyroscope is a MEMS gyroscope.

8. The device of claim 1, further comprising:
at least one pressure sensor configured to sense a pressure difference between a pressure in ear canal (PEC) of a user and an ambient pressure (PAMB), wherein the active valve is configured to open and close the vent at least in part based on an output of the at least one pressure sensor.

9. The device of claim 8, wherein the at least one pressure sensor is a differential pressure sensor.

10. The device of claim 8, wherein the at least one pressure sensor comprises a first sensor configured to sense the PEC, and a second sensor configured to sense the PAMB.

11. A method for equalizing air pressure in an ear canal, the method comprising:
touching a touch sensor by a user, wherein the touch sensor is configured to sense handling of a hearing device, wherein the touch sensor is operationally connected with a controller of the hearing device, and wherein the touch sensor is carried by a removal handle that is attached to a housing of the hearing device; and
in response to touching the touch sensor, setting an active valve of the hearing device to a first position to open a vent through the hearing device or to a second position to close the vent through the hearing device.

12. The method of claim 11, wherein the removal handle connects an in-the-ear piece with a behind-the-ear piece of the hearing device.

13. The method of claim 11, further comprising:
keeping the active valve of the hearing device open for a predetermined duration of time.

14. The method of claim 11, further comprising:
sensing a movement of a hearing device within the ear canal by a movement detection sensor; and
based at least in part on sensing the movement, setting an active valve of the hearing device to the first position to open a vent through the hearing device or to the second position to close the vent through the hearing device.

15. The method of claim 14, wherein the movement detection sensor is an accelerometer.

16. The method of claim 14, wherein the movement detection sensor is a gyroscope.

17. The method of claim 11, further comprising:
detecting a pressure difference between a pressure in ear canal ($P_{EC}$) and an ambient pressure ($P_{AMB}$) by a pressure sensor of the hearing device; and
based at least in part on sensing the pressure difference, setting the active valve to the first position or to the second position.

18. The method of claim 17, wherein the pressure sensor is a differential pressure sensor configured to sense the pressure difference between the $P_{EC}$ and the $P_{AMB}$.

19. The method of claim 17, wherein the pressure sensor comprises a first pressure sensor, configured to sense a first environmental condition corresponding to the $P_{EC}$ and a second pressure sensor configured to sense a second environmental condition corresponding to the $P_{AMB}$, the method further comprising:
determining a difference between the first environmental condition and the second environmental condition.

20. The method of claim 11, wherein the hearing device is selected from a group consisting of a completely-in-ear-canal (CIC) hearing device, a receiver-in-canal (RIC) hearing device, a behind-the-ear (BTE) hearing device, an in-the-ear (ITE) hearing device, an audio reproduction device, a hearable, an earphone, and a hearing assistive device.

* * * * *